United States Patent
Jing et al.

(10) Patent No.: US 10,539,158 B2
(45) Date of Patent: Jan. 21, 2020

(54) BLOWER DEVICE AND RESPIRATOR INCLUDING BLOWER DEVICE

(71) Applicant: BMC Medical Co., Ltd., Beijing (CN)

(72) Inventors: Bowei Jing, Beijing (CN); Shumin Gao, Beijing (CN); Zhi Zhuang, Beijing (CN)

(73) Assignee: BMC Medical Co., Ltd., Beijing (CN)

(*) Notice: Subject to any disclaimer, the term of this patent is extended or adjusted under 35 U.S.C. 154(b) by 533 days.

(21) Appl. No.: 15/197,147

(22) Filed: Jun. 29, 2016

(65) Prior Publication Data

US 2016/0312801 A1 Oct. 27, 2016

Related U.S. Application Data

(63) Continuation of application No. PCT/CN2014/091579, filed on Nov. 19, 2014.

(30) Foreign Application Priority Data

Jan. 3, 2014 (CN) .......................... 2014 1 0003968

(51) Int. Cl.
*F04D 29/66* (2006.01)
*A61M 16/00* (2006.01)
(Continued)

(52) U.S. Cl.
CPC .......... *F04D 29/668* (2013.01); *A61M 16/00* (2013.01); *A61M 16/0066* (2013.01);
(Continued)

(58) Field of Classification Search
CPC .... F04D 29/668; F04D 29/4233; F04D 17/16; A61M 16/00; A61M 16/0066; A61M 2205/42
See application file for complete search history.

(56) References Cited

U.S. PATENT DOCUMENTS 4,978,281 A * 12/1990 Conger, IV ........... F04D 25/082
264/271.1
5,823,753 A 10/1998 Kemmerling
(Continued)

FOREIGN PATENT DOCUMENTS

CN 2203371 Y 7/1995
CN 1856649 A 11/2006
(Continued)

OTHER PUBLICATIONS

First Chinese Office Action from counterpart Chinese Application CN103807221A.
(Continued)

*Primary Examiner* — Brian P Wolcott
(74) *Attorney, Agent, or Firm* — Flener IP & Business Law; Zareefa B. Flener

(57) ABSTRACT

A blower device and a respirator including the blower device. The blower device comprises a case, a blower vibration source disposed within the case and a buffering assembly for associating the blower vibration source and the case, wherein the vibration absorption assembly comprises at least two of a locating buffering member associated with a top portion of the blower vibration source, a connection buffering member in which at least a part of the blower vibration source is received and a support buffering member associated with a bottom portion of the blower vibration source. The blower device is capable of effectively buffering vibration of the blower device, decreasing noise transmission and has a simple structure.

11 Claims, 4 Drawing Sheets

(51) Int. Cl.
    *F04D 17/16* (2006.01)
    *F04D 29/42* (2006.01)
(52) U.S. Cl.
    CPC ......... *F04D 17/16* (2013.01); *F04D 29/4233* (2013.01); *A61M 2205/42* (2013.01)

(56) References Cited

U.S. PATENT DOCUMENTS

| | | | |
|---|---|---|---|
| 6,315,526 B1 * | 11/2001 | Jones | A61M 16/0057 417/363 |
| 6,371,738 B2 | 4/2002 | Jones | |
| 7,617,823 B2 * | 11/2009 | DiMatteo | A61M 16/0066 128/204.18 |
| 7,975,688 B1 * | 7/2011 | Truitt | A61M 16/0066 128/200.24 |
| 9,044,559 B2 * | 6/2015 | Grasmuck | A61M 16/0066 |
| 2007/0020120 A1 | 1/2007 | Oh et al. | |
| 2007/0048159 A1 | 3/2007 | DiMatteo et al. | |
| 2008/0304986 A1 * | 12/2008 | Kenyon | A61M 16/0066 417/423.12 |
| 2009/0301485 A1 | 12/2009 | Kenyon et al. | |
| 2013/0343926 A1 * | 12/2013 | Wykman | B60N 2/5621 417/363 |

FOREIGN PATENT DOCUMENTS

| | | | | |
|---|---|---|---|---|
| CN | 1856649 A1 | 11/2006 | | |
| CN | 202791248 U | 3/2013 | | |
| CN | 103429289 A | 12/2013 | | |
| CN | 103807221 A | 5/2014 | | |
| CN | 103807221 A | 5/2014 | | |
| DE | 4107049 A1 | 9/1992 | | |
| EP | 1912486 A1 * | 4/2008 | ........... | F04D 29/601 |
| FR | 2953142 A1 | 6/2011 | | |
| FR | 2953142 A1 | 6/2011 | | |
| WO | 00/48293 A1 | 8/2000 | | |
| WO | WO00/48293 A1 | 8/2000 | | |
| WO | WO 2005028870 A1 * | 3/2005 | ........... | F04B 39/0044 |

OTHER PUBLICATIONS

Second Chinese Office Action from counterpart Chinese Application CN103807221A, dated May 5, 2016.
Third Chinese Office Action from counterpart Chinese Application CN103807221A, dated Oct. 10, 2016.
European Search Report from counterpart European Application EP3901238A1, dated Nov. 7, 2016.
International Search Report for counterpart PCT Application PCT/CN2014/091579, dated Feb. 27, 2015.
Written Opinion from counterpart PCT Application PCT/CN2014/091579, dated Feb. 27, 2015.

* cited by examiner

BLOWER DEVICE AND RESPIRATOR INCLUDING BLOWER DEVICE

CROSS-REFERENCE TO RELATED APPLICATIONS

The present application is a continuation of PCT international application No. PCT/CN2014/091579 filed on Nov. 19, 2014, which claims priority to Chinese Patent Application No. 201410003968.X, filed on Jan. 3, 2014, titled "Blower Device and Respirator Including Blower Device", in the State Intellectual Property Office of China, all contents of these applications are incorporated by reference herein.

TECHNICAL FIELD

The present invention relates to a small-sized blower device, more particularly to a blower device having improved vibration absorption function. The present invention also relates to a respirator including such a blower device.

BACKGROUND

As an important component in a respirator, a blower is used to generate gas for breathing and deliver the gas to patients. During rotation of a blower with a high speed, blades of the blower cut air with a high speed so as to produce air flow vibration. The air flow vibration will be transmitted to the blower. Thus, operation of the blower with a high speed will result in high-frequency vibration. Frequency and amplitude of the vibration are spread outwards, which causes a lot of secondary damages, such as life reduction of a component, vibration and noise radiated from the device, and so on.

In order to minimalize the secondary damages, special protective treatments are required for the vibration of the blower. However, a large number of components will be added to implement the special protective treatments, resulting in a very complicated structure of the blower. Moreover, in the prior art, usually a blower with special protective treatments is connected and located via rigid connections, which has adverse influence on high-frequency vibration of the blower and decrease of noise transmission due to the vibration.

SUMMARY

The technical problem to be solved by the present invention is to provide a blower device which is capable of effectively buffering vibration of the blower, decreasing noise transmission and has a simple structure.

A technical solution of the present invention is to provide a blower device comprising a case, a blower vibration source disposed within the case and a vibration absorption assembly for associating the blower vibration source and the case, wherein the vibration absorption assembly comprises at least two of a locating buffering member associated with a top portion of the blower vibration source, a connection buffering member in which at least a part of the blower vibration source is received and a support buffering member associated with a bottom portion of the blower vibration source.

Compared with the prior art, the present invention has the following advantages: combination of two or three of the locating buffering member, the connection buffering member and the support buffering member functions as connection, locating and buffering for the blower vibration source. An amplitude of high-frequency vibration of the blower vibration source during operation is buffered, and noise transmission out of the case due to the high-frequency vibration is decreased, thereby effectively reducing secondary damage. Moreover, there are a small number of components, thus the structure is simple and the assembling is easy.

In an embodiment, the locating buffering member comprises a locating ring disposed at the top portion of the blower vibration source and a locating seat which is provided at the case and is used to receive the locating ring. Cooperation between the locating ring disposed at the top portion of the blower vibration source and the locating seat provided at the case functions as limiting displacement and buffering for the blower vibration source, thus not only lateral movement of the blower vibration source due to high-frequency vibration can be controlled, but also a portion of vibration can be effectively dispersed.

In a preferred embodiment, the blower device comprises a plurality of support buffering members which are uniformly disposed on a bottom surface of the connection buffering member. The plurality of support buffering members can effectively disperse vibration of the blower vibration source.

In a further preferred embodiment, each of the support buffering members comprises a support pillar extended from the bottom surface of the connection buffering member and three support legs which are spaced apart from each other and are extended from an end surface of the support pillar, the support legs collectively form a horn-shaped component extended and gradually expanded from the end surface of the support pillar, and are received in a respective receiving groove disposed at a bottom wall of the case. The support buffering members having such a structure can maximize dispersion of vibration of the blower vibration source, and provide a stable support. Cooperation between the support buffering members and the receiving grooves can effectively limit rotation and downward movement of the blower vibration source.

In a preferred embodiment, rigid stoppers are provided between adjacent ones of the support pillars, the rigid stoppers are provided at the bottom surface of the connection buffering member and extended more from the bottom surface of the connection buffering member than the support pillars. When the blower vibration source produces excessive vibration, the rigid stoppers will be brought into contact with a bottom surface of the lower case, thereby limiting further downward movement of the blower vibration source.

In a preferred embodiment, the blower vibration source comprises a blower seal ring tightly connected with the case. The blower seal ring can effectively reduce an amplitude of high-frequency vibration of the blower vibration source.

In another embodiment, the vibration absorption assembly comprises the locating buffering member associated with the top portion of the blower vibration source and the connection buffering member in which at least a part of the blower vibration source is received, the connection buffering member is configured as being hung within the case. Such a structure benefits dispersion of vibration energy and decrease of noise.

In a preferred embodiment, the connection buffering member comprises a connection part extended horizontally from a side wall of the connection buffering member, the case comprises a circumferential platform located at an inner side wall of the case, and the connection part is supported on the circumferential platform via a tapered support part. The circumferential support table can buffer and disperse high-frequency vibration of the blower vibration source more effectively.

In yet another embodiment, the connection buffering member comprises a hook-shaped connection part extended horizontally from a side wall of the connection buffering member, the case comprises a hook support part located at an inner side wall of the case, and the hook-shaped connection part is hung on the hook support part. Such a connection structure is relatively simple, but also benefits dispersing of high-frequency vibration of the blower vibration source.

In yet another embodiment, the connection buffering member is configured as a box body in which the blower vibration source is completely received, the locating buffering member comprises buffering members fixed on a top portion of the connection buffering member and extended to the case with cross-sections being gradually decreased, and the support buffering member comprises buffering members fixed on a bottom portion of the connection buffering member and extended to a bottom wall of the case with cross-sections being gradually decreased. By combining the connection buffering member having a box body and the support buffering member, the high-frequency vibration can be buffered and the secondary damage can be reduced greatly.

In yet another embodiment, the connection buffering member is configured as a box body in which the blower vibration source is completely received, the locating buffering member comprises buffering members fixed on a top wall of the case and extended to the connection buffering member with cross-sections being gradually decreased, and the support buffering member comprises buffering members fixed on a bottom wall of the case and extended to the connection buffering member with cross-sections being gradually decreased. Combination of the connection buffering member having a box body, the tapered locating buffering member and the tapered support buffering member can effectively locate and buffer the blower vibration source, thus maximizing buffering of the high-frequency vibration and reducing secondary damage.

In a preferred embodiment, the connection buffering member comprises a hook-shaped connection part extended horizontally from a side wall of the connection buffering member, the case comprises a hook support part located at an inner side wall of the case, and the hook-shaped connection part is hung on the hook support part. The connection between the hook-shaped connection part and the hook support part enables hanging the blower vibration source within the case, a vibration amplitude of the blower vibration source is buffered and limited in both an up and down direction and a left and right direction, thus effectively dispersing high-frequency vibration of the blower vibration source and reducing noise.

In yet another embodiment, the connection buffering member is configured as a box body in which the blower vibration source is completely received, the support buffering member comprises a buffering block connected to a bottom surface of the box body and bottom wall buffering members extended from a bottom surface of the buffering block with cross-sections being gradually decreased. Combination of the buffering block and the bottom wall buffering members can effectively disperse high-frequency of the blower vibration source and limit a downward vibration amplitude of the blower vibration source.

In a preferred embodiment, the case comprises an upper case and a lower case which are engaged with each other, the connection buffering member comprises a connection part extended from a side wall of the connection buffering member, and the connection part is pressed between engagement surfaces of the upper case and the lower case. This structure is simple.

In yet another embodiment, the vibration absorption assembly comprises the locating buffering member associated with the top portion of the blower vibration source and the support buffering member associated with the bottom portion of the blower vibration source, the support buffering member comprises a support pillar extended through a bottom wall of the case, a clamping block and a support leg are provided at two ends of the support pillar respectively, a buffering material is filled in an opening through which the support pillar passes the case. The support buffering member limits a magnitude of downward movement of the blower vibration source, and the locating buffering member limits lateral movement of the blower vibration source in a certain extent. Combination of the locating buffering member and the support buffering member can disperse high-frequency vibration of the blower vibration source.

In a preferred embodiment, the locating buffering member, the connection buffering member and the support buffering member are made of silicone. Silicone materials can play a role in supporting and buffering.

The present invention also relates to a respirator comprising a blower device as described above.

DETAILED DESCRIPTION

Hereinafter the present invention will be described in detail with reference to the accompanying drawings and the specific embodiments.

Figure 1:
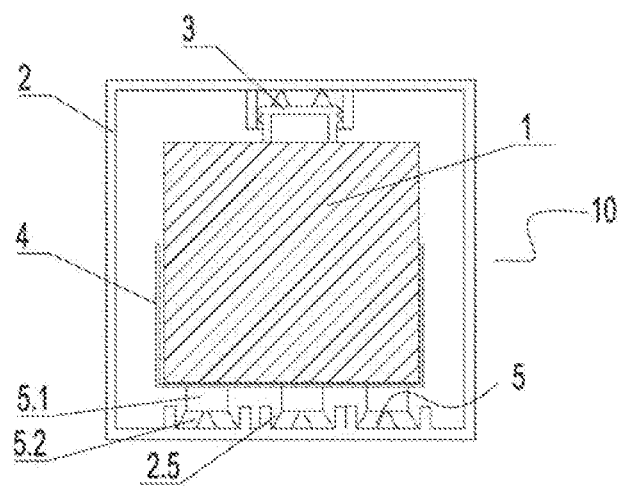
FIG. 1 schematically illustrates a structure of a blower device according to a first embodiment of the present invention.

First, a blower device 10 according to a first embodiment of the present invention will be described with reference to FIGS. 1-4. As shown in FIG. 1, the device 10 comprises a case 2 and a blower vibration source 1 mounted in the case 2. The blower vibration source 1 is, for example, a motor of the blower device. Those skilled in the art will readily appreciate that the blower device 10 also includes some other conventional components, which are well known in the art and thus detailed description thereof will be omitted herein.

According to the present invention, a locating buffering member 3 is disposed at a top portion of the blower vibration source 1, and is used to connect the blower vibration source 1 to an inner side of a top wall of the case 2. In this embodiment, as more clearly shown in FIG. 4, the locating buffering member 3 may include a locating ring 3.1 which is extended into a corresponding locating seat 2.4 disposed at the inner side of the top wall of the case 2. The locating seat 2.4 is configured to have an inner diameter which is slightly larger than an outer diameter of the locating ring 3.1, so that point contact or line contact can be formed between the locating ring 3.1 and the locating seat 2.4. In addition, the locating ring 3.1 may be disposed at the top portion of the blower vibration source 1 via a well-known structure, such as a complementary engagement projection-groove structure. By providing the locating ring 3.1, not only lateral movement of the blower vibration source 1 due to high-frequency vibration can be controlled, but also a portion of vibration can be effectively dispersed.

According to the present invention, the blower device 10 includes a connection buffering member 4 associated with the blower vibration source 1. In the first embodiment of the present invention, the connection buffering member 4 is configured as a cylindrical component in which at least a part of the blower vibration source 1 is received. The blower device 10 also includes a support buffering member 5 for supporting the connection buffering member 4 in which at least a part of the blower vibration source 1 is received on a bottom wall of the case 2.

Figure 3:
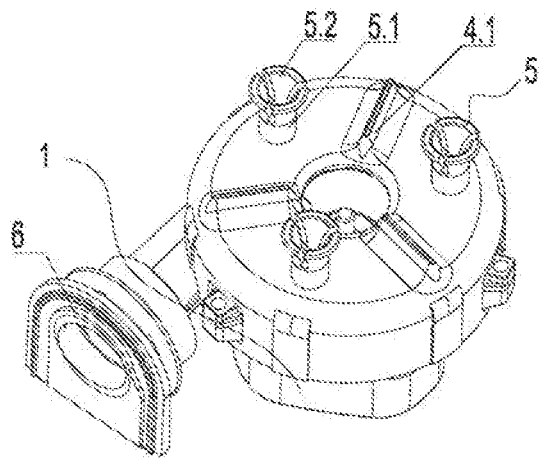
FIG. 3 is a schematic bottom view of the structure shown in FIG. 2.

FIG. 3 illustrates the support buffering member 5 clearly. As shown, in the first embodiment of the present invention, the blower device 10 includes three support buffering members 5 which are preferably arranged uniformly in a circumferential direction. It will be readily understood that more support buffering members 5 may be disposed as required. Each of the support buffering members 5 comprises a support pillar 5.1 extended outwards from a bottom end of the connection buffering member 4 and three support legs 5.2 which are spaced apart from each other and extended outwards from an end surface of the support pillar 5.1. The three support legs 5.2 of each of the support buffering members 5 collectively form a horn-shaped part extended and expanded gradually from the end surface of the support pillar 5.1. The three support legs 5.2 of each of the support buffering members 5 are received in a respective receiving groove 2.5 (referring to FIG. 4) disposed on a bottom surface of the case 2. Preferably, the receiving grooves 2.5 each is sized and shaped to just receive the three support legs 5.2. By providing the support buffering members 5 each having three independent support legs 5.2, vibration from the blower vibration source 1 can be effectively dispersed. In addition, in the case of the blower vibration source 1 producing a downward displacement, the receiving grooves 2.5 can limit each of the support legs 5.2 inside, thereby limiting downward movement and freedom of rotation of the blower vibration source 1.

The above-mentioned locating buffering member 3 and the connection buffering member 4 are made of a material which can provide buffering function. For example, they may be made of a silicone material. For the support buffering member 5, at least the support legs 5.2 are made of a material which can provide buffering function, e.g., a silicone material. The support pillars 5.1 may be made of a rigid material such as plastic, alternatively it may be made of a silicone material.

Figure 4:
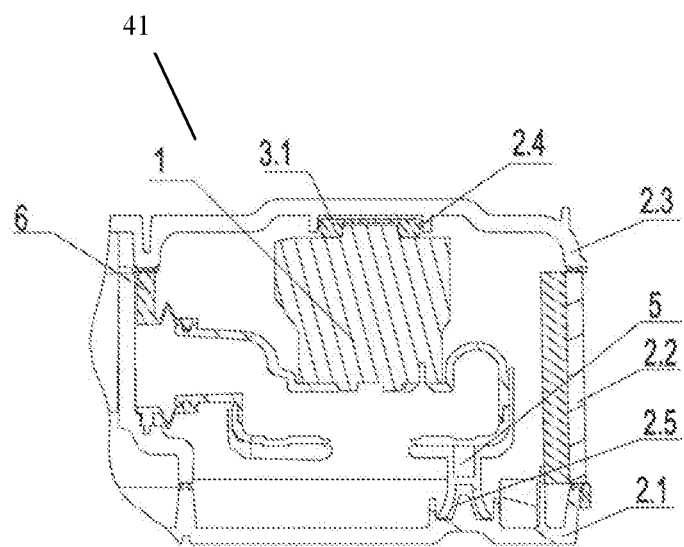
FIG. 4 is a sectional view along plane A shown in FIG. 2 according to the first embodiment, in which some components are omitted for clarity.

According to a specific embodiment of the present invention, as shown in FIG. 4, the case 2 may include a lower case 2.1, a middle case 2.2 and an upper case 2.3. Here, the locating seat 2.4 is disposed at the upper case 2.3, and the receiving grooves 2.5 are disposed at the lower case 2.1. Compared with a case having an integral structure, the case having this three-part structure can disperse the high-frequency vibration from the blower vibration source 1 more effectively.

Figure 2:
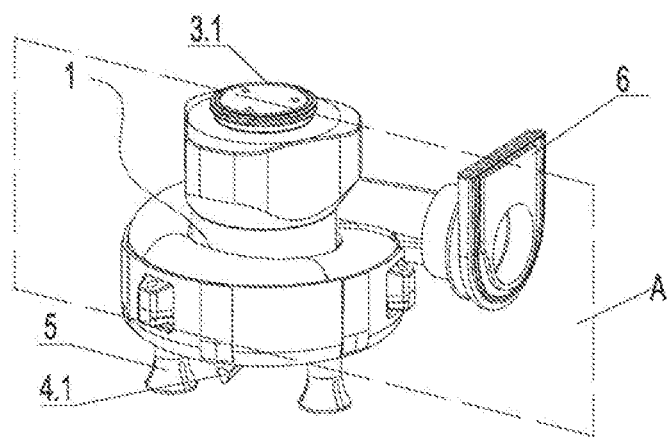
FIG. 2 is a perspective view illustrating the blower device shown in FIG. 1 with a case being removed.

According to a preferred embodiment of the present invention, as shown in FIG. 2, a blower seal ring 6 is connected with the blower vibration source 1, and is tightly connected with the case 2, specifically the middle case 2.2. After the blower vibration source 1 is mounted into the case 2, the blower seal ring 6 can function as limiting rotation of the blower vibration source 1. In addition, a thin-walled butterfly-shaped vibration absorbing structure may be provided in the blower seal ring 6, so that an amplitude of high-frequency vibration of the blower vibration source 1 can be effectively dispersed.

As shown in FIG. 3, rigid stoppers 4.1 can be provided optionally on a bottom surface of the connection buffering member 4. In the illustrated embodiment, each of three rigid stoppers 4.1 is arranged between two adjacent support buffering members 5. The rigid stoppers 4.1 are configured to be extended further than the support pillars 5.1 of the support buffering member 5. Thus, when the blower vibration source 1 produces excessive vibration, the rigid stoppers 4.1 will be brought into contact with a bottom surface of the lower case 2.1, thereby limiting further downward movement of the blower vibration source 1.

Hereinafter the blower devices according to the second to the seventh embodiments will be described with reference to FIGS. 5-10. In order to avoid redundancy, only differences from the first embodiment shown in FIGS. 1-4 will be described and repeated description can be referred to the description above.

Figure 5:
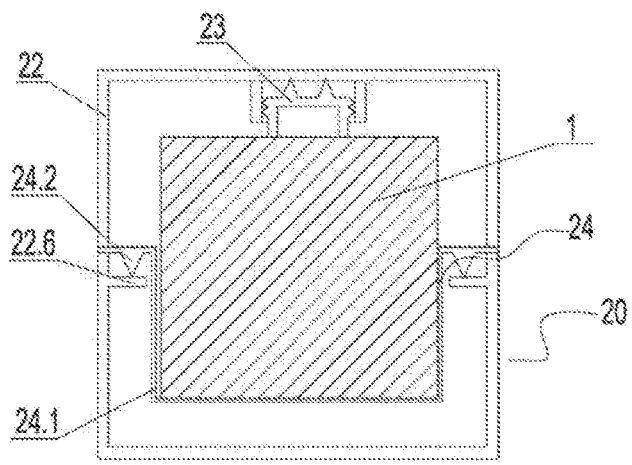
FIG. 5 schematically illustrates a structure of a blower device according to a second embodiment of the present invention.

FIG. 5 illustrates a blower device 20 according to a second embodiment of the present invention. In the second embodiment, the blower device 20 does not include the support buffering member 5 shown in the first embodiment. However, a connection buffering member 24 of the blower device 20 includes a cylindrical part 24.1 in which at least a part of the blower vibration source 1 is received and a connection part 24.2 extended horizontally from a peripheral wall of the cylindrical part 24.1 The connection part 24.2 is supported on a support platform 22.6 disposed at an inner wall of a case 22. For example, the connection part 24.2 can be supported on the support platform 22.6 via a structure with reduced contact surface (such as a tapered portion). The cylindrical part 24.1 and the connection part 24.2 each is made of a material which can provide buffering function, e.g., a silicone material. Thus, in the second embodiment, the blower vibration source 1 is actually hung in the case 22 via the connection buffering member 24. In this case, vibration of the blower vibration source 1 can be dispersed effectively by a locating buffering member 23 and the connection buffering member 24.

Figure 6:
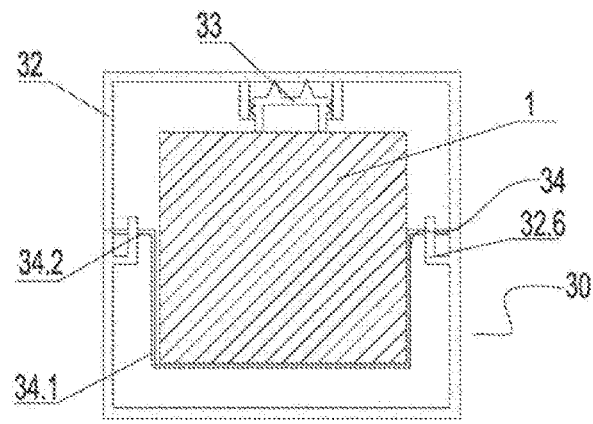
FIG. 6 schematically illustrates a structure of a blower device according to a third embodiment of the present invention.

FIG. 6 illustrates a blower device 30 according to a third embodiment of the present invention. The blower device 30 is substantially the same as the blower device 20 according to the second embodiment shown in FIG. 5. The difference lies in that, in the blower device 30, a connection part 34.2 and an inner wall of a case 32 are engaged with each other via a hook structure. Specifically, a hook support part 32.6 is provided at the inner wall of the case 32, and a free end of the connection part 34.2 is configured as a hook which can be hung on the hook support part 32.6. In this way, the blower vibration source 1 can be hung within the case 32 reliably, which will benefit dispersion of vibration energy.

Figure 7:
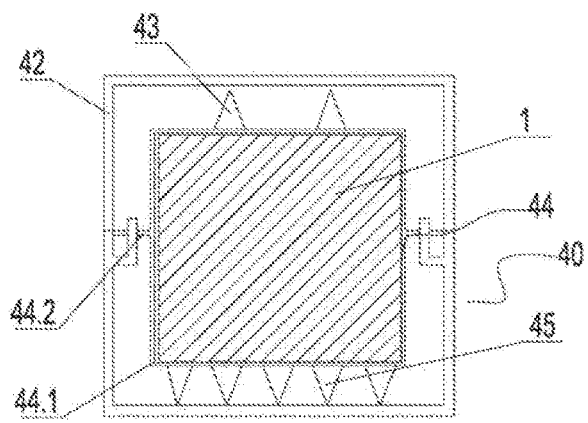
FIG. 7 schematically illustrates a structure of a blower device according to a fourth embodiment of the present invention.

FIG. 7 illustrates a blower device 40 according to a fourth embodiment of the present invention. In this embodiment, the connection buffering member 44 is configured as a box body, and a blower vibration source 41 is completely received in the connection buffering member 44. In addition, a locating buffering member 43 and a support buffering member 45 are integrated with a top surface and a bottom surface of the connection buffering member 44 respectively. The locating buffering member 43 and the support buffering member 45 may have the same structures as those in the first embodiment, alternatively they may be simple tapered buffering members, so that point contact or line contact is formed between the buffering members and the case. In addition, a connection part 44.2 similar to the connection part shown in FIG. 6 may be provided at a side wall of the connection buffering member 44, and is used to form hook engagement with an inner wall of a case 42.

Figure 8:
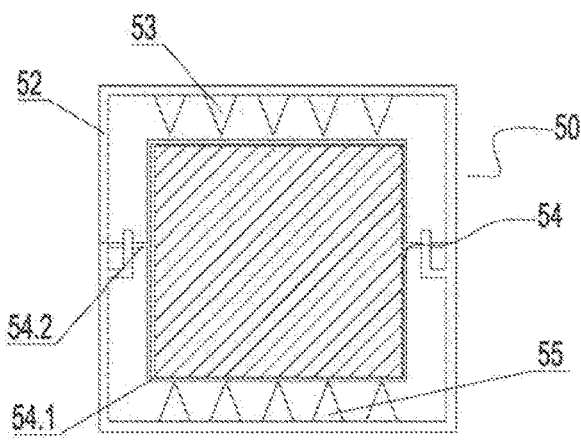
FIG. 8 schematically illustrates a structure of a blower device according to a fifth embodiment of the present invention.

FIG. 8 illustrates a blower device 50 according to a fifth embodiment of the present invention. In this embodiment, the connection buffering member 54 has the same structure as the fourth embodiment. However, a locating buffering member 53 and a support buffering member 55 are not provided on the connection buffering member 44, rather they are provided on a top wall and a bottom wall of a case 52 respectively. The locating buffering member 53 and the support buffering member 55 are configured as tapered buffering members, so that point contact or line contact is formed between them and the case 52.

Figure 9:
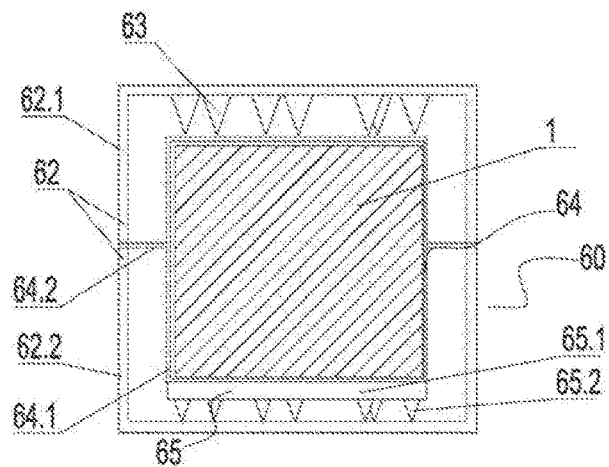
FIG. 9 schematically illustrates a structure of a blower device according to a sixth embodiment of the present invention.

FIG. 9 illustrates a blower device 60 according to a sixth embodiment of the present invention. In this embodiment, a case 62 is configured to include an upper case 62.1 and a lower case 62.2. A locating buffering member 63 is disposed on a top wall of the upper case 62.1, and has point contact or line contact with a top wall of a box-shaped connection buffering member 64. A support buffering member 65 is connected to a bottom wall of the connection buffering member 64 via a buffering block 65.1, and a bottom surface of the buffering block 65.1 is connected to bottom wall buffering members 65.2 which each has gradually reduced cross-section toward a bottom wall of the lower case 62.2. Preferably, the buffering block 65.1 and the bottom wall buffering members 65.2 are formed integrally.

Moreover, point contact or line contact is formed between each of the bottom wall buffering members 65.2 and the bottom wall of the lower case 62.2. The connection buffering member 64 also comprises a connection part 64.2 extended horizontally from the side wall of the connection buffering member 64, and the connection part 64.2 is pressed between engagement surfaces of the upper case 62.1 and the lower case 62.2.

Figure 10:
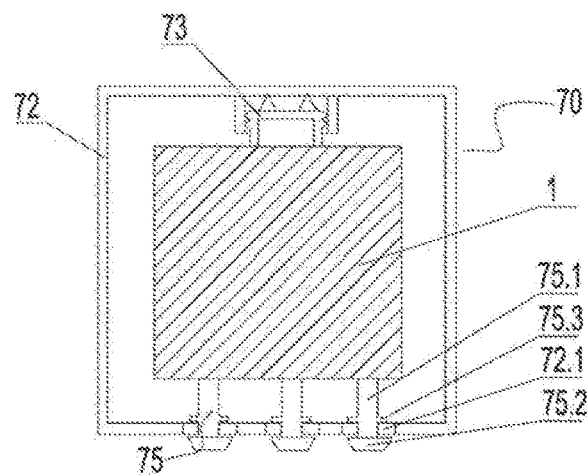
FIG. 10 schematically illustrates a structure of a blower device according to a seventh embodiment of the present invention.

FIG. 10 illustrates a blower device 70 according to a seventh embodiment of the present invention. In this embodiment, the blower device 70 includes a locating buffering member 73 similar to that according to the first embodiment, however it doesn't include a connection buffering member. In addition, the blower device 70 includes support buffering members 75 extended outwards from a bottom surface of a blower vibration source 71. The support buffering members 75 each includes a support pillar 75.1 extended through a case 72 and a support leg 75.2 disposed at a free end of a side of the support pillar 75.1 which is outside the case 72. In order to prevent each of the support buffering members 75 from dropping out from the case 72, a clamping block 75.3 is provided at another side of the support pillar 75.1 which is inside the case 72. In this embodiment, buffering members 72.1 which are made of, for example, silicon are respectively provided at places through which the support pillars 75.1 pass the case 72. And there is a small gap between each of the buffering members 72.1 and the respective clamping block 75.3 and/or the respective support leg 75.2, so that a better buffering function is provided.

Although the present invention has been described with reference to specific embodiments, it will be understood that various changes and modifications can be made within the scope of the present invention. In particular, various features of the above-described embodiments can be mixed provided that there is no conflict in structure, and the combined technical features still fall into the scope of the present invention. Therefore, the present invention is not limited to the embodiments disclosed herein, rather, all technical schemes within the scope of the claims are covered.

What is claimed is:

1. A blower device, comprising a case, a blower vibration source disposed within the case and a vibration absorption assembly for associating the blower vibration source and the case, wherein the vibration absorption assembly comprises a locating buffering member associated with a top portion of the blower vibration source and a connection buffering member in which at least a part of the blower vibration source is received;

wherein the connection buffering member is configured as being hung within the case; wherein the connection buffering member comprises a connection part extended horizontally from a side wall of the connection buffering member, the case comprises a circumferential platform located at an inner side wall of the case, and the connection part is supported on the circumferential platform via a tapered support part.

2. The blower device according to claim 1, wherein the locating buffering member comprises a locating ring disposed at the top portion of the blower vibration source and a locating seat which is provided at an inner side of a top portion of the case and is used to receive the locating ring.

3. The blower device according to claim 1, wherein the blower vibration source comprises a blower seal ring tightly connected with the case.

4. The blower device according to claim 1, wherein the connection buffering member comprises a hook-shaped connection part extended horizontally from a side wall of the connection buffering member, the case comprises a hook support part located at an inner side wall of the case, and the hook-shaped connection part is hung on the hook support part.

5. The blower device according to claim 1, wherein the connection buffering member is configured as a box body in which the blower vibration source is completely received, and the locating buffering member comprises buffering members fixed on a top portion of the connection buffering member and wherein the buffering members of the locating buffering member are extended to the case with cross-sections being gradually decreased.

6. The blower device according to claim 5, wherein the connection buffering member comprises a hook-shaped connection part extended horizontally from a side wall of the connection buffering member, the case comprises a hook support part located at an inner side wall of the case, and the hook-shaped connection part is hung on the hook support part.

7. The blower device according to claim 1, wherein the connection buffering member is configured as a box body in which the blower vibration source is completely received, and the locating buffering member comprises buffering members fixed on a top wall of the case and wherein the buffering members of the locating buffering member are extended to the connection buffering member with cross-sections being gradually decreased.

8. The blower device according to claim 7, wherein the connection buffering member comprises a hook-shaped connection part extended horizontally from a side wall of the connection buffering member, the case comprises a hook support part located at an inner side wall of the case, and the hook-shaped connection part is hung on the hook support part.

9. The blower device according to claim 1, wherein the connection buffering member is configured as a box body in which the blower vibration source is completely received.

10. The blower device according to claim 9, wherein the case comprises an upper case and a lower case which are engaged with each other, the connection buffering member comprises a connection part extended from a side wall of the connection buffering member, and the connection part is pressed between engagement surfaces of the upper case and the lower case.

11. A respirator, comprising a blower device which comprises a case, a blower vibration source disposed within the case and a vibration absorption assembly for associating the blower vibration source and the case, wherein the vibration absorption assembly comprises a locating buffering member associated with a top portion of the blower vibration source; and a connection buffering member in which at least a part of the blower vibration source is received;

wherein the connection buffering member is configured as being hung within the case; wherein the connection buffering member comprises a connection part extended horizontally from a side wall of the connection buffering member, the case comprises a circumferential platform located at an inner side wall of the case, and the connection part is supported on the circumferential platform via a tapered support part.

* * * * *